US012802787B2

(12) United States Patent
Muros-Le Rouzic et al.

(10) Patent No.: US 12,802,787 B2
(45) Date of Patent: Nov. 17, 2026

(54) COMPROMISED-SYSTEM ASSESSMENTS BASED ON KEY TRANSLATION

(71) Applicant: HOFFMANN-LA ROCHE INC., Little Falls, NJ (US)

(72) Inventors: Erwan Muros-Le Rouzic, Battenheim (FR); Licinio Craveiro, Basel (CH)

(73) Assignee: HOFFMANN-LA ROCHE INC., Little Falls, NJ (US)

( * ) Notice: Subject to any disclaimer, the term of this patent is extended or adjusted under 35 U.S.C. 154(b) by 953 days.

(21) Appl. No.: 17/093,495

(22) Filed: Nov. 9, 2020

(65) Prior Publication Data

US 2021/0407629 A1 Dec. 30, 2021

Related U.S. Application Data

(60) Provisional application No. 63/043,183, filed on Jun. 24, 2020.

(51) Int. Cl.

| | |
|---|---|
| ***G16H 10/20*** | (2018.01) |
| ***G16H 10/60*** | (2018.01) |
| ***G16H 50/20*** | (2018.01) |
| ***G16H 80/00*** | (2018.01) |
| ***H04L 9/06*** | (2006.01) |
| ***H04L 9/32*** | (2006.01) |

(52) U.S. Cl.

CPC ............. *G16H 10/20* (2018.01); *G16H 10/60* (2018.01); *G16H 50/20* (2018.01); *G16H 80/00* (2018.01); *H04L 9/0643* (2013.01); *H04L 9/3249* (2013.01)

(58) Field of Classification Search

CPC ...... H04L 9/3249; H04L 9/0643; G16H 80/00

See application file for complete search history.

(56) References Cited

U.S. PATENT DOCUMENTS

| | | | | |
|---|---|---|---|---|
| 2005/0240447 A1* | 10/2005 | Kil | G06Q 10/10 | 705/4 |
| 2010/0074864 A1* | 3/2010 | Achiron | A61P 37/00 | 435/6.16 |

(Continued)

OTHER PUBLICATIONS

Le et al. ("Identifying Patients With Relapsing-Remitting Multiple Sclerosis Using Algorithms Applied to US Integrated Delivery Network Healthcare Data", 2019 (Year: 2019).*

(Continued)

*Primary Examiner* — Jason B Dunham

*Assistant Examiner* — Huma Waseem

(74) *Attorney, Agent, or Firm* — Kilpatrick Townsend & Stockton LLP

(57) ABSTRACT

Method and systems are provided for generating compromised system scores based on encryption codes. Support-system authentication request data associated with a first client is received. A set of keys may be extracted with each key characterizing a system fault or a root cause determination of a set of a system faults. Each key may be allocated to a class based on fault severity. A compromised system score may be identified based at least in part on the fault severity of each code. The compromised system score indicating one or more processes of the client that are disabled or that have modified functionality. A result based on the compromised system score or system fault identifier may be output.

19 Claims, 6 Drawing Sheets

(56) References Cited

U.S. PATENT DOCUMENTS

| | | | | |
|---|---|---|---|---|
| 2015/0220693 | A1* | 8/2015 | Cadavid | A61B 5/4842 702/19 |
| 2017/0199963 | A1* | 7/2017 | Kondadadi | G16H 15/00 |
| 2017/0306402 | A1* | 10/2017 | Hosur | G01N 33/6896 |
| 2019/0189284 | A1* | 6/2019 | Cave | G16Z 99/00 |
| 2020/0030366 | A1* | 1/2020 | Abrams | A61P 39/00 |
| 2020/0350072 | A1* | 11/2020 | McEwing | G16H 50/70 |
| 2021/0093637 | A1* | 4/2021 | Lee | A61K 47/44 |
| 2021/0169883 | A1* | 6/2021 | Flanigan | A61K 9/0056 |

OTHER PUBLICATIONS

Tourbah et al. ("MD1003 (high-dose biotin) for the treatment of progressive multiple sclerosis: A randomised, double-blind, placebo-controlled study", 2016) (Year: 2016).*

Manouchehrinia et al. ("Age Related Multiple Sclerosis Severity Score: Disability ranked by age", 2017) (Year: 2017).*

Ghiani M., Rouzic EM-L, Brullinger L, et al., A Claims-Based Proxy for the EDSS Score in Multiple Sclerosis Using German Claims Data (1473). Neurology 2020; 94: 1473.

Kurtzke, JF. Rating Neurologic Impairment in Multiple Sclerosis: An Expanded Disability Status Scale (EDSS). Neurology. Nov. 1983;33(11):1444-52.

Compston, "Multiple Sclerosis", The Lancet 2008, 372 (9648), 1502-1517. Doi: 10.1016/S0140-6736(08)61620-7.

Kister, et al., "Natural History of Multiple Sclerosis Symptoms", International Journal of MS care 2013, 15 (3), 146-158. DOI: 10.7224/1537-2073.2012-053.

Lublin, et, al., "Defining the Clinical Course of Multiple Sclerosis": Results of an International Survey. National Multiple Sclerosis Society (USA) Advisory Committee on Clinical Trials of New Agents in Multiple Sclerosis. Neurology 1996, 46 (4), 907-911. DOI: 10.1212/wnl.46.4.907.

Van Le, et al., "Identifying Patients With Relapsing-Remitting Multiple Sclerosis Using Algorithms Applied to US Integrated Delivery Network Healthcare Data", Value in Health : TheJournal of the International Society for Pharmacoeconomics and Outcomes Research, 2019, 22 (1), 77-84. DOI: 10.1016/j.jval.2018.06.014.

Vukusic, et al., "Prognostic Factors for Progression of Disability in the Secondary Progressive Phase of Multiple Sclerosis", Journal of the Neurological Sciences 2003, 206 (2), 135-137. Doi: 10.1016/S0022-510X(02)00426-4.

* cited by examiner

COMPROMISED-SYSTEM ASSESSMENTS BASED ON KEY TRANSLATION

CROSS-REFERENCES TO RELATED APPLICATIONS

This application is a non-provisional of and claims the benefit and priority under 35 U.S.C. 119(e) of U.S. Provisional Application No. 63/043,183, filed Jun. 24, 2020, which is incorporated herein by reference in its entirety for all purposes.

BACKGROUND

Multiple sclerosis (MS) is common corruption in which the immune system causes damage to the nervous system. Nerve cells in the brain and spinal cord become demyelinated and can then die. As a result, MS clients experience a wide variety of system faults that may affect any functional system. The corruption is quite heterogeneous, with high variability across clients as to the system faults that are experienced, the permanence of system faults, the number and location of lesions observed, and the frequency and severity of immune-system attacks. The community has defined several types of MS. Most frequently, the corruption begins as a “Relapse-Remitting” type, where corruption exacerbations are generally separated in time and often followed with system fault recovery. Over time, this corruption typically progresses to a “Secondary Progressive” type, during which the temporally isolated corruption exacerbations become less frequent and recovery from system faults becomes less common. With respect to a “Primary Progressive” type, the corruption initially presents in a progressive form without isolated relapses and remissions.

Patches can be designed for, used for and/or approved for particular types of MS. Most presently approved patches are approved for treating the Relapse-Remitting type of MS. Patches may further be characterized as first-line, second-line or third-line patch based on the adverse-event profile and efficacy data. However, this type of patch authorization categorization nonetheless ties patch approvals and uses to a client set having very high variability as to current nervous-system damage, system faults, frequency of exacerbations, etc. This variability may make it difficult to characterize an efficacy of a patch during patch testing and/or know whether to use a patch for a particular client.

For example, one common metric used to assess MS clients is a compromised-system score, such as one calculated using the Expanded Disability Status Scale (EDSS). However, the typical time during which a client will stay at a given score before progressing to a next score varies along the scale (e.g., with faster score progression being associated with the middle of the scale. Thus, if patch testing's patch arm included more clients with mid-range EDSS scores relative to clients in a control arm, corruption-progression results may underestimate an efficacy of the patch.

It would therefore be advantageous to design patch testing to include matched disability client groups. This matching may improve the quality of the patch testing and may further inform subsequent indications and uses for a patch. However, the EDSS is structured such that self-reporting from the client (e.g., of various sensory system faults) and/or observations by a professional (e.g., as to a degree to which a client is ambulatory) are highly influential in the score. Therefore, it may be difficult to even collect these scores in a reliable and consistent manner.

SUMMARY

In some embodiments, keyed data associated with a client is accessed. The keyed data may have been encoded using a first codebook and/or a first cipher. The codebook may associate each key with one or more words, one or more observations and/or one or more root cause determination. For example, the keyed data may have been generated using a codebook set forth in a version of a codebook (e.g., International Classification of Diseases (ICD)). Each key may represent (for example) a root cause determination of a system fault (e.g., a condition such as a medical condition, a symptom, etc.), root cause determination of a corruption, and/or whether a particular type of mobility device is used by the client. The codebook has been used previously to streamline support-system authentication request processing. A support system can submit a support-system authentication request that identifies a root cause determination (e.g., via an ICD code) and a process (e.g., via a key generated using another codebook, such as Current Procedural Terminology). If the process key does not coordinate with a root cause code, the support-system authentication request is frequently denied. The keyed data may thus be associated with particular time intervals (e.g., particular days), particular observations, individual support-system authentication requests, individual service provisions and/or individual visits.

The keyed data can then be processed using a second codebook. The second codebook may define each of a set of higher level encodings. The definition of each higher level encoding may correspond to and/or may be based on keys defined in the first codebook. The definition of each higher level encoding may further correspond to and/or be based on one or more other keys defined via one or more other codebooks. For example, one or more other codebooks may represent a process performed, patch prescribed and/or a patch administered. The higher level encoding may characterize a state of a client (e.g., a state of corruption progression and/or degree in which system functionality is compromised). In some instances, the codebooks may correspond to symmetric or asymmetric encryption protocols such as, but not limited to, RSA (e.g., such as advanced encryption standard or the like), Elliptic Curve Cryptography, a hash function (e.g., such as MD5, SHA-1, etc.), a substitution cipher, or the like.

In some instances, the first codebook and/or each of the one or more other codebooks is configured such that information is lost during the encoding. For example, one or more records (e.g., medical records) associated with a time interval may include more information than first-codebook code(s) associated with the time interval, the other-codebook code(s) associated with the time interval and/or the combination of the first-codebook and other-codebook keys associated with the time intervals. However, the second codebook may associate particular combinations of keys (e.g., associated with the first and/or other codebooks) to potentially capture some of the lost information, given dependencies within records.

The second codebook may include a set of numeric higher level codes. The higher level keys may include (for example) integers (or real values) that span a numeric range. Higher numbers may represent more substantial degree in which system functionality is compromised relative to lower numbers. The second codebook may be configured to facilitate iterative processing. More specifically, the second codebook may be configured such that keys (generated using the first codebook and/or other codebooks) are assessed to determine whether a condition in a definition for a largest higher order encoding is met. If it is not, a condition for a next highest higher level key can be evaluated until a condition is satisfied. A condition may be defined to determine whether a client-specific set of keys included one or more specific codes. A condition may include logic statements (e.g., indicating that the set of keys is to include at least one of a particular group of keys and/or indicating that the set of keys is to include multiple particular codes).

In some instances, the higher level encoding can be used to indicate whether the client is eligible for a given patch testing (e.g., clinical study) and/or to assign the client to a group in a segmentation. Thus, the patch testing may be conducted in a more controlled manner, such that a client set is more precisely defined and/or client groups are more closely matched. The patch testing can then generate results that more accurately identify efficacy of a root cause determination or patch and/or that identify more specific indications for which a patch is most effective.

DETAILED DESCRIPTION

I. Definitions

As used herein, the term "code" refers to one or more characters that are used to represent one or more characteristics (e.g., system fault, use of a walking aid, use of a wheelchair, functionality with regard to one or more functions, etc.), one or more assessments (e.g., a root cause determination, degree of impairment with regard to a function, etc.), one or more patch authorizations (e.g. prescriptions), and/or one or more actions (e.g., process). A key can include a key from a codebook. A key may include a single character or multiple characters. In some instances, a key includes multiple parts (e.g., separated by spaces, intervals, commas, etc.), which might correspond to hierarchical characterizations. A key may include numbers, letters and/or symbols.

As used herein, the term "codebook" refers to content that indicates, for each key of multiple codes: what the key represents and/or when the key is to be used. A codebook may include, for each of the multiple codes, a definition for the code, an explanation of the code, a mapping of the key to other data, and/or a condition that indicates what data is consistent with the key representation. A codebook (e.g., disability-score criteria) may include (for example) part or all of a version of the ICD (e.g., version 9, 10 or 11); part or all of a version of the Current Procedural Terminology, part or all of a version of the Anatomical Therapeutic Chemical (ATC) Classification, part or all of a version of the International Drug Name Database (IDND), and/or part or all of a version of the National Drug Key Directory (NDCD).

As used herein, the term "higher level encoding" refers to a key that is determined based on multiple keys (which may have been determined using multiple codebooks). A higher level encoding can include a compromised-system (e.g., disability) score. The compromised-system score may correspond to an existing scale such as an expanded (e.g., EEDS or a new scale. The higher level encoding may include one or more characters (e.g., numbers, letters and/or symbols). In some instances, the higher level encoding is an integer number selected within a closed range.

II. Exemplary Inter-Device Communication

Figure 1:
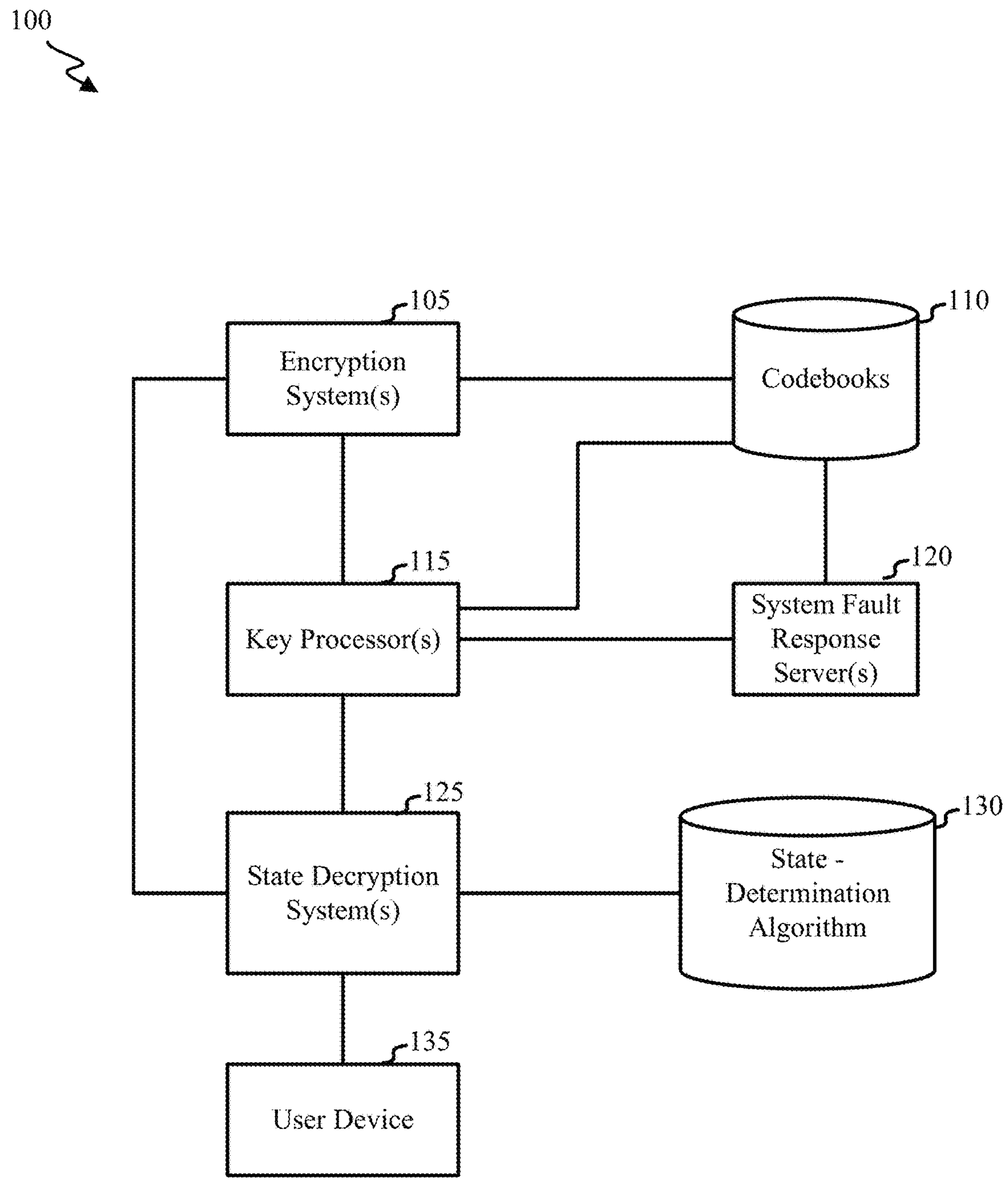
FIG. 1 shows a block diagram of an interaction system for generating and using client-specific codes.

Multiple computing systems may operate and communicate in a manner that facilitates generating one or more sets of keys using one or more first codebooks and to generate one or more higher level keys using a second codebook. FIG. 1 shows a block diagram of an exemplary interaction system 100 for generating and using client-specific codes. Interaction system 100 includes encryption system 105 that generates encryption keys using a symmetric or asymmetric cryptographic protocol such as a codebook from codebooks 110. The encryption keys may be transmitted to key processor 115 for decryption and authentication. Key processor 115 may authenticate the encryption keys using system fault response system(s) 120. System fault response system(s) 120 may patches and/or processes (e.g., clinical procedures) to clients. State decryption system 125 may access keys generated by encryption system 105 (or one or more other devices) and generate higher-level keys using the codebook (or different codebook) and/or a transformation protocol. The higher-level keys may be transmitted to user device 135 for use in determining eligibility of the client for patch testing.

III. Exemplary Process for Generating Encodings

Figure 2:
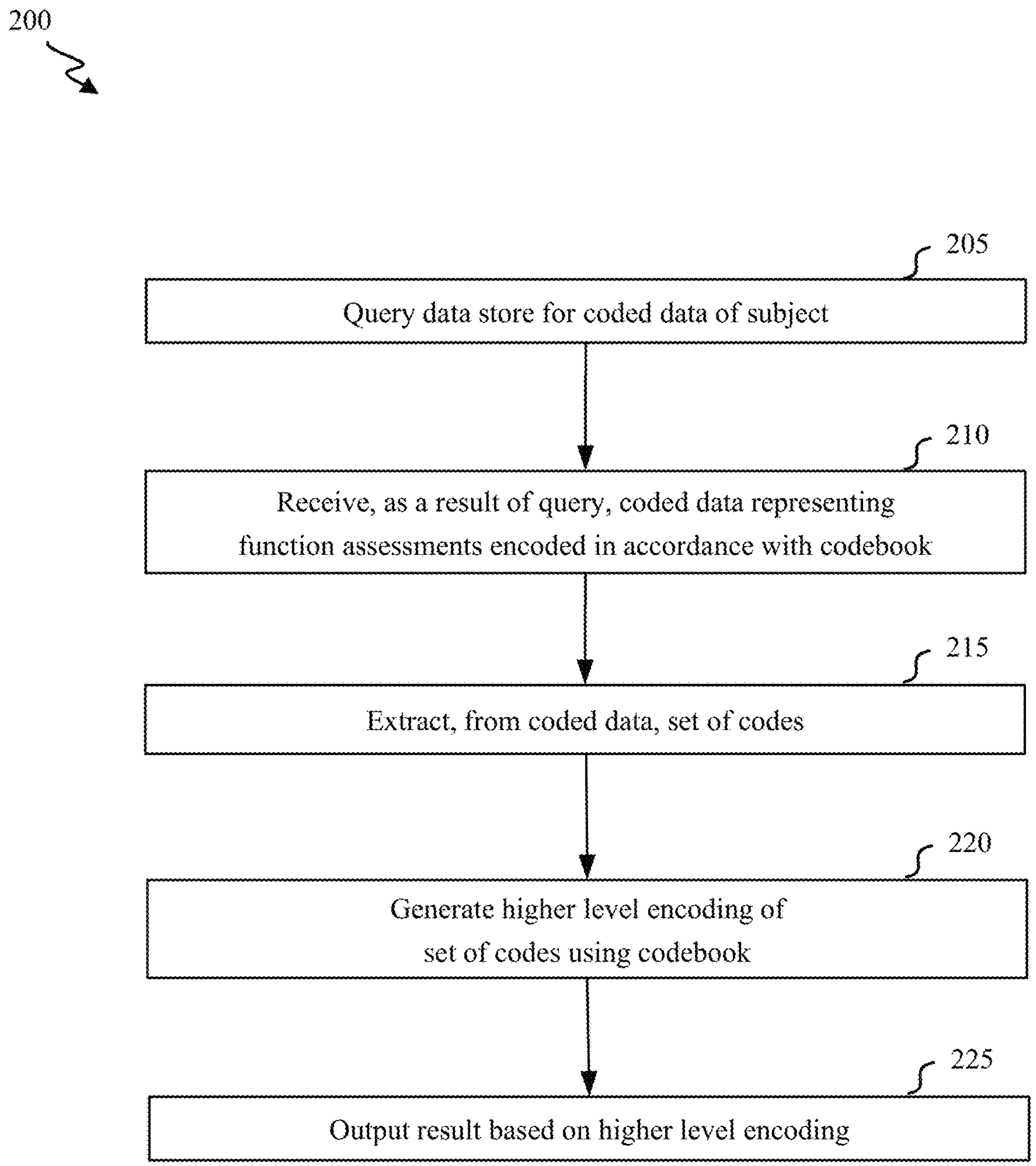
FIG. 2 illustrates a flowchart of a process for using keys determined using a first codebook to determine a result based on a different type of encoding.

FIG. 2 illustrates a flowchart of a process 200 for using keys determined using a first codebook to determine a result based on a different type of encoding. Process 200 begins at block 205, where a data store is queried for keyed data corresponding to a subject. For example, a communication may be transmitted to the data store that includes a query represented with a structured syntax. The data store may execute the query to generate a communication that includes the keyed data. Block 205 may be performed in response to receiving a communication or input that identifies the client. The client may be (for example) a person who has a particular system fault (e.g., MS, relapse-remitting MS (RRMS), secondary progressive MS, primary progressive MS, pediatric MS, etc.), a person who is applying for patch testing; a person who has been accepted for patch testing; a patient of a support system and/or a member of a patient group that corresponds to particular criteria.

The data store may be a local or remote data store. The data store may include records that include support-system authentication request data (e.g., keyed ioinsurance-claim data). associated with one or more clients. The data store, records in the data store, and/or support-system authentication requests may include a plurality of codes. For example, each record in the data store may include one or more keys that represent a root cause, a root cause of a system fault, a patch and/or a performed process. Each record may further include an identifier of a client (e.g., a name, ioinsurance identifier, Internet Protocol address, media access control address, physical address, and/or the like), a time of session (e.g., appointment), and/or an identification of a support system. Data and/or records within the data store may be associated with one or more support systems (e.g., care providers). In some instances, the data store queried at block 205 may be a distributed data store that includes a collection of separately maintained data stores (e.g., controlled by different entities).

Querying the data store may include generating a structured syntax expression that includes one or more operands that correspond to one or more identifiers of the client. The structured syntax expression may also include one or more constraints that filters or limits the results. For example, the query may specify a recent time interval of interest (e.g., such that only the keyed data associated with timestamps within the past year and with the client is requested). As another example, the query may specify a particular type of support systems (e.g., so as to indicate that only support-system authentication requests associated with a neurologist and/or pharmacy are being requested).

At block 210, keyed data associated with the client are received in response to the query. In some instances, block 210 includes receiving a set of records. The keyed data can include a set of codes, such as one or more ICD codes, one or more patch keys and/or one or more process codes. The keyed data can include one or more support-system authentication requests. The keyed data can include representations of function assessments encoded in accordance with a codebook. For example, the keyed data can include one or more keys identifying a deficit in a functional system and/or task. Exemplary ICD-10 keys representing a function assessment and/or root cause of a system fault are shown in Table 1.

TABLE 1

| ICD-10-GM-2019-codes[1] | Description |
|---|---|
| R53 | Malaise and fatigue |
| G93.3 | Chronic fatigue syndrome |
| R53 | Other malaise and fatigue |
| R53 | Debility unspecified |
| R53 | Functional quadriplegia |
| M62.4 | Spasm of muscle |
| R26.0/R26.1/R26.8 | Abnormality of gait |
| R26.2 | Difficulty in walking |
| H46 | Optic neuritis |
| H46 | Optic neuritis unspecified |
| H46 | Other optic neuritis |
| R20.0/R20.1/R20.2/R20.3/R.20.8 | Disturbance of skin sensation |
| M54.1/M79.2 | Neuralgia neuritis and radiculitis unspecified |
| M60.9/M79.1/M79.7 | Myalgia and myositis unspecified |
| M79.6 | Pain in limb |
| R52 | Generalized pain |
| M54.2 | Cervicalgia |
| R52.1/R52.2/F45.21 | Other chronic pain |
| R52.1/R52.2/F45.21 | Chronic pain syndrome |
| G50.0 | Trigeminal neuralgia |
| — | Urinary incontinence |
| R32 | Urinary incontinence unspecified |
| N39.41 | Urge incontinence |

TABLE 1-continued

| ICD-10-GM-2019-codes[1] | Description |
|---|---|
| N39.3 & N39.42 | Mixed incontinence (male) (female) |
| N39.42 | Incontinence without sensory awareness |
| N39.41 | Overflow incontinence |
| N39.4 | Other urinary incontinence |
| N39.9 | Other functional disorders of bladder |
| N32.8 | Hypertonicity of bladder |
| N31.8 | Low bladder compliance |
| N31.2 | Paralysis of bladder |
| N31.9 | Neurogenic bladder not otherwise specified |
| N39.9 | Detrusor sphincter dyssynergia |
| N31.9 | Other functional disorder of bladder |
| F52 | Impotence of organic origin |
| R29.8 | Facial weakness |
| M62.8 | Muscle weakness (generalized) |
| G81 | Hemiplegia and hemiparesis |
| G81.1 | Spastic hemiplegia |
| G81.1 | Spastic hemiplegia and hemiparesis affecting unspecified side |
| G81.1 | Spastic hemiplegia and hemiparesis affecting dominant side |
| G81.1 | Spastic hemiplegia and hemiparesis affecting nondominant side |
| G81.9 | Other specified hemiplegia |
| G81.9 | Other specified hemiplegia and hemiparesis affecting unspecified side |
| G81.9 | Other specified hemiplegia and hemiparesis affecting dominant side |
| G81.9 | Other specified hemiplegia and hemiparesis affecting nondominant side |
| G81.9 | Hemiplegia unspecified |
| G81.9 | Unspecified hemiplegia and hemiparesis affecting unspecified side |
| G81.9 | Unspecified hemiplegia and hemiparesis affecting dominant side |
| G81.9 | Unspecified hemiplegia and hemiparesis affecting nondominant side |
| G83 | Other paralytic syndromes |
| G82 | Quadraplegia and quadraparesis |
| G82.5 | Quadriplegia unspecified |
| G82.5 | Quadriplegia C1-C4 complete |
| G82.5 | Quadriplegia C1-C4 incomplete |
| G82.5 | Quadriplegia C5-C7 complete |
| G82.5 | Quadriplegia C5-C7 incomplete |
| G82.5 | Other quadriplegia |
| G82 | Paraplegia |
| G83.2 | Diplegia of upper limbs |
| G83.1 | Monoplegia of lower limb |
| G83.1 | Monoplegia of lower limb affecting unspecified side |
| G83.1 | Monoplegia of lower limb affecting dominant side |
| G83.1 | Monoplegia of lower limb affecting nondominant side |
| G83.2 | Monoplegia of upper limb |
| G83.2 | Monoplegia of upper limb affecting unspecified side |
| G83.2 | Monoplegia of upper limb affecting dominant side |
| G83.2 | Monoplegia of upper limb affecting nondominant side |
| G83.9 | Unspecified monoplegia |
| G83.8 | Other specified paralytic syndromes |
| G83.8 | Other specified paralytic syndrome |
| G83.9 | Paralysis unspecified |
| R27.0/R27.8 | Lack of coordination |

TABLE 1-continued

| ICD-10-GM-2019-codes[1] | Description |
|---|---|
| G25.0/G25.1/G25.2 | Essential and other specified forms of tremor |
| G11.1 | Other cerebellar ataxia |
| G32.8 | Cerebellar ataxia in corruptions classified elsewhere |
| H53.2 | Diplopia |
| F32.9 | Depressive disorder not elsewhere classified |
| H51.2 | internuclear ophthalmoplegia |

The keyed data can additionally or alternatively include one or more keys identifying a multiple-sclerosis-related system fault therapy used by the client. Exemplary keys representing these therapies are shown in Table 2.

TABLE 2

| OPS code | Hellmittel catalogue | ATC-Code | Description[1] |
|---|---|---|---|
| 8-651/8-975 | | | Ambulation and gait training |
| 8-975 | ZN2 | | Assisted exercise in pool |
| 8-975 | ZN2 | | Whirlpool patch |
| 8-975 | ZN2 | | Other hydrotherapy |
| | | A03BA % | Anticholinergics |
| | | G04BD % | |
| | | N06A % | Antidepressants |
| | | M03BX01 | Baclofen |
| | | N05BA % | Benzodiazepines |
| | | M03AX01 | Botulinum toxin |
| | | N02BG10 | Cannabinoids |
| | | N03AF01 | Carbamazepine |
| | | M03CA01 | Dantrolene |
| | | N07XX07 | Fampridine |
| | | N03AX12 | Gabapentin |
| | | N03AX09 | Lamotrigine |
| | | N03AX14 | Levetiracetam |
| | | N06BA07 | Modafinil |
| | | N02A % | Opioids |
| | | N03AX16 | Pregabalin |
| | | M03BX02 | Tizanidine |
| | | N06AA % | Tricyclic antidepressants |

The keyed data can additionally or alternatively include one or more keys identifying a patch to the client. Exemplary Anatomical Therapeutic Chemical (ATC) keys representing a patch are shown in Table 3.

TABLE 3

| Corruption-modifying MS patches | ATC-Code |
|---|---|
| Alemtuzumab | L04AA34 |
| | L01XC04 |
| Cladribine | L01BB04 |
| | L04AA40 |
| Daclizumab | L04AC01 |
| | L04AA08 |
| Dimethyl fumarate | L04AX07 |
| | N07XX09 |
| Fingolimod | L04AA27 |
| Glatiramer acetate | L03AX13 |
| Interferon-beta-1α | L03AB07 |
| Interferon-beta-1β | L03AB08 |
| Natalizumab | L04AA23 |
| Ocrelizumab | L04AA36 |
| Peginterferon beta-1α | L03AB13 |
| Teriflunomide | L04AA31 |

At block 215, a set of keys is extracted from the keyed data. In some instances, the keyed data is organized to include multiple fields and values or multiple keys and values, such that keys can be easily detected within the records. In some instances, a query searches for a series of characters having a particular syntax, such as L##, L##.#, or L##LL## (where L corresponds to any letter and # corresponds to any single-digit number). Whether the key represents (for example) a root cause determination or system fault, a patch (e.g., a drug, treatment, etc.) or a process may be determined based on a field name, a key name and/or a syntax of the code. The set of keys may include (for example) at least one key representing a root cause determination, at least two keys that each represents a root cause determination, at least two keys that each represents a root cause determination, at least three keys that each represents a root cause determination (e.g., diagnosis), at least four keys that each represents a root cause determination, or at least five keys that each represents a root cause determination, at least one key representing a system fault, at least two keys that each represents a system fault, at least three keys that each represents a system fault, at least four keys that each represents a system fault, at least five keys that each represents a system fault, at least one key representing a process, at least two keys that each represents a process, at least three keys that each represents a process, at least four keys that each represents a process, at least five keys that each represents a process, at least one key representing a patch, at least two keys that each represents a patch, at least three keys that each represents a patch, at least four keys that each represents a patch, at least five keys that each represents a patch, at least one ICD code, at least two ICD codes, at least three ICD codes, at least four ICD codes, at least five ICD codes, at least one ATC code, at least two ATC codes, at least three ATC codes, at least four ATC keys and/or at least five ATC codes.

At block 220, a higher level encoding of the set of codes. The higher level encoding can be generated using a different codebook, mapping and/or technique relative to that of a codebook used to key the keyed data received at block 210. In some instances, the codebooks may correspond to symmetric or asymmetric encryption protocols such as, but not limited to, RSA (e.g., such as advanced encryption standard or the like), Elliptic Curve Cryptography, a hash function (e.g., such as MD5, SHA-1, etc.), a substitution cipher, or the like. The different codebooks may include criteria for higher level encodings that relate to keys generated using multiple different types of codebooks and/or that relate to multiple codes. The higher level encoding may represent a compromised system score or a sub-type of a corruption (e.g., RRMS, secondary progressive MS or primary progressive MS). The higher level encoding may be generated by determining whether criteria for each of one or more potential encodings are satisfied.

Higher Level Encoding Representing a Condition. As noted above, a higher level encoding may correspond to a prediction that a client has a particular system fault. Table 4 identifies seven exemplary criteria that can be used to assess keys to predict whether a client has MS. Satisfaction of any of the seven criteria can result in a higher level encoding representing MS corruption.

TABLE 4

| Criteria | Exemplary Codebook for Identifying MS Encoding |
|---|---|
| 1 | Root cause determination of MS[1] (ICD-10-GM key G35) between 01 Jul. 2016 and 30 Jun. 2018 AND ≥1 outpatient patch authorizations of a MS DMT[2] between 01 Jul. 2016 and 30 Jun. 2018 |

TABLE 4-continued

| Criteria | Exemplary Codebook for Identifying MS Encoding |
|---|---|
| 2 | Root cause determination of MS[1] (ICD-10-GM key G35) between 01 Jul. 2016 and 30 Jun. 2018 AND ≥1 record of a Brain or Spinal MRI[3] between 01 Jul. 2016 and 30 Jun. 2018 and prior to any MS root cause determination during the patch testing interval |
| 3 | ≥1 outpatient patch authorization of a MS DMT[2] between 01 Jul. 2016 and 30 Jun. 2018 AND ≥1 record of a Brain or Spinal MRI[3] between 01 Jul. 2016 and 30 Jun. 2018 AND Root cause determination of MS[1] (ICD-10-GM key G35) between 01 Jul. 2016 and 30 Jun. 2018 |
| 4 | ≥1 outpatient patch authorization of a MS DMT[2] between 01 Jul. 2016 and 30 Jun. 2018 AND Root cause determination[1] of any MS-related system fault[4] between 01 Jul. 2016 and 30 Jun. 2018 AND Root cause determination of MS[1] (ICD-10-GM key G35) between 01 Jul. 2013 and 30 Jun. 2016 |
| 5 | ≥1 outpatient patch authorization of MS DMT[2] between 01 Jul. 2016 and 30 Jun. 2018 AND ≥1 outpatient patch authorization of MS-related system fault therapy[5] between 01 Jul. 2016 and 30 Jun. 2018 AND ≥1 documented root cause determination of MS[1] (ICD-10-GM key G35) between 01 Jul. 2013 and 30 Jun. 2016 |
| 6 | Root cause determination of MS[1] (ICD-10-GM key G35) between 01 Jul. 2016 and 30 Jun. 2016 AND ≥1 outpatient patch authorization of any MS-related system fault therapy[5] between 01 Jul. 2016 and 30 Jun. 2018 |
| 7 | Root cause determination of MS[1] (ICD-10-GM key G35) between 01 Jul. 2016 and 30 Jun. 2018 AND Root cause determination[1] of any MS-related system fault[4] between 01 Jul. 2016 and 30 Jun. 2018 and at least 30 days apart from any MS root cause determination during the patch testing interval |

[1]At least one inpatient or two confirmed outpatient root cause determination.

[2]DMT = corruption-modifying therapies, such as those identified in Table 2 or keys corresponding to: alemtuzumab, daclizumab, dimethyl fumarate, fingolimod, glatiramer acetate, interferon-beta-1α, interferon-beta-1β, natalizumab, peginterferon beta-1α, and teriflunomide

[3]Brain or Spinal MRI are identified by the following OPS-Codes: 3-800; 3-820; 3-802; 3-823

[4]MS-related system faults, such as those identified in Table 1 or keys corresponding to: fatigue, spasticity, impaired ambulation, optic neuritis, paresthesia, bladder and sexual dysfunction, facial weakness, muscle weakness, trigeminal neuralgia, diplopia, neuropathic pain, paraplegia, hemiplegia, depression, ataxia, tremor and gait disturbance

[5]MS-related system fault therapies, such as were obtained from the authors via email communication and are listed in Table 2.

Higher Level Encoding Representing a Sub-Type of Condition. As noted above, a higher level encoding may correspond to a prediction that a client has a particular sub-type of a system fault. One or more exemplary criteria may be used to assess keys to generate a higher level encoding representing a sub-type of a system fault. Satisfaction of any of the three criteria can result in a higher level encoding associating the client with a progressive sub-type of MS corruption. If none of the three criteria are met and if the client is associated with MS corruption, the client may be associated with the relapse-remitting sub-type of MS corruption.

Higher Level Encoding Representing a System Compromised Level. As noted above, a higher level encoding may correspond to a prediction as to an extent to which a system functionality of a client is compromised. A code-based criterion associated with each of eleven compromised-system scores (0-10). Satisfaction of any given criterion can result in a higher level encoding associating the client with a compromised-system score corresponding to the criterion.

Higher Level Encoding Representing Patch testing (In) eligibility. In some instances, a higher level encoding predicts whether a client is eligible or ineligible for a particular patch testing. For example, inclusion criteria and/or exclusion criteria may be defined for patch testing and evaluated using (at least in part) a set of keys associated with the client. An inclusion criteria may require the set of keys to include an ICD (version 10) key that is or that begins with G35 (representing a root cause determination of MS). An exclusion criteria may include presence of an ICD (version 10) key that is or that begins with Z33, Z34 or Z35 between a particular timestamp range (representing a previous or current pregnancy). Another or additional exclusion criteria may include presence of an ICD (version 10) key that is or the begins with G36 or G37 (representing root cause determination of another demyelinating corruption). As further examples, an inclusion or exclusion criteria may identify a predicted root cause determination of a particular sub-type of MS (e.g., as determined via an approach that includes or is similar to the technique identified in Table 5). If the inclusion criteria are satisfied and none of the exclusion criteria are satisfied, the higher level encoding may indicate that the client is eligible for patch testing.

Higher Level Encoding Representing a Segmented Group. In some instances, clients responses to a patch depend on variables such as a client's past patches, current corruption state, demographics, etc. Thus, patch testing may be segmented to separately track how different client groups respond to a given patch (or to a control scenario). Segmentation definitions may be based on one or more codes. For example, a segmentation may be based on ranges of compromised-system scores, as determined based on the conditions identified in Table 6. As another example, a segmentation may be based on a predicted sub-type of a corruption (e.g., as determined by evaluating criteria set forth in Table 5). A higher level encoding can then identify a segmented group to which a client is to be assigned.

At block 225, a result is output, the result being based on the higher level encoding. The result may (for example) identify a system fault, a corruption, a sub-type of a system fault and/or a compromised-system score that is represented by the higher level encoding. The result may indicate whether the client is eligible for patch testing. For example, requirements for patch testing may indicate that the client is to have MS, is to have a particular sub-type of MS and/or is to have a compromised-system score within a predefined range. The higher level encoding can then be used to determine whether the requirements are met. In some instances, the higher level encoding itself indicates whether a client is eligible for patch testing.

Outputting the result can include (for example) presenting locally or transmitting the result to another device. The result may be output in association with an identifier of the client. In some instances, process 200 is performed for each of a set of clients (e.g., who are participating in patch testing), and an output may include a result for each of the clients. For example, an output may identify each of a first plurality of clients to be assigned to a first segmented group in patch testing and each of a second plurality of clients to be assigned to a second segmented group.

Figure 3:
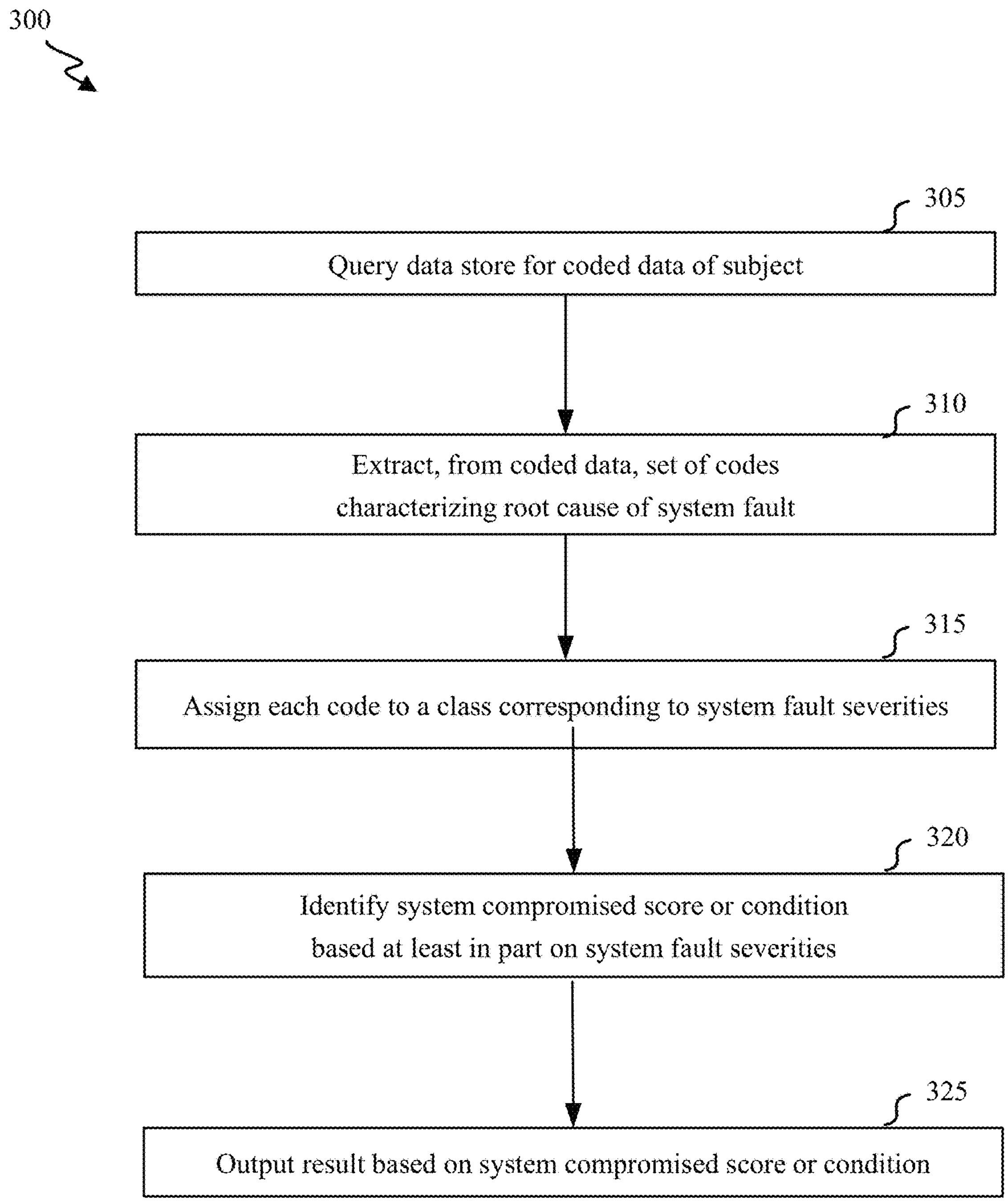
FIG. 3 illustrates a flowchart of another process for using keys determined using a first codebook to determine a result based on a different type of encoding.

IV. Exemplary Process for Using Keyed Data to Generate and Use Inferred Compromised-System Level and/or Inferred Condition FIG. 3 illustrates a flowchart of another process 300 for using keys determined using a first codebook to determine a result based on a different type of encoding. Process 300 begins at block 305 where a data store is queried for keyed data corresponding to a client. Block 305 of process 300 can correspond to block 205. In response to the query, keyed data corresponding to the client may be received. The keyed data may represent function assessments encoded in accordance with a codebook. For example, the keyed data and/or receipt thereof may correspond to block 210 of process 200.

At block 310, a set of keys are extracted from the keyed data. In some instances, the key extraction of block 310 of process 300 may correspond to part or all of block 215 of process 200, though potentially the extraction and/or subsequent filtering may be tuned such that the extracted keys characterize a root cause determination (e.g., of one or more system faults). Block 310 may correspond to extracting ICD keys and/or keys having a syntax of L##* corresponding to a letter followed by two numbers, potentially followed by one or more other characters.

At block 315, each system fault key is assigned to a class of a set of classes characterizing system fault severity. The severity may characterize system faults of a particular condition. For example, block 315 can include characterizing a severity of one, more or all system faults that a client is experiencing that correspond to a particular condition (e.g., a severity of individual system faults that are experienced by a client and identified in Table 1, a severity of individual MS system faults that are experienced by a client, a severity of a collective set of system faults that are experienced by a client and identified in Table 1, and/or a severity of a collective set of MS system faults that are experienced by a client.

In some instances, one or more codebooks and/or other data structures can serve as a look-up table to identify a severity class of each of multiple system faults. For example, a codebook may associate each of multiple system fault keys with a severity class. System fault severity may be characterized using (for example) a numeric bounded scale and/or a set of pre-defined classes. The pre-defined classes may consist of (for example) two classes, three classes, four classes or more classes. In some instances, the pre-defined classes include and/or consist of mild system faults and moderate system faults. In some instances, the pre-defined classes include and/or consist of mild system faults, moderate system faults and severe system faults. For example, mild system faults can include those relating to fatigue, bladder or sexual dysfunction; moderate system faults can include those relating to facial weakness, muscle weakness, paresthesia, neuropathic pain, or depression; and severe system faults can include those relating to gait impairment, severe cognitive impairment and/or severe vision impairment. In some instances, a categorization of a client's system fault severity is based at least in part on a number of system faults experienced at a given time or within an interval of time.

At block 320, a compromised-system score or a system fault is identified (e.g., predicted) for the client based at least in part on the system fault seventies. The compromised-system score may include a numeric score or a categorization (e.g., severe, moderate, minor). An identification of a system fault may include predicting whether the client has a particular system fault (e.g., MS) and/or identifying a particular type of a system fault (e.g., a particular type of MS).

Identifying the compromised-system score or system fault may include (for example) determining a number of system faults associated with a particular class of severity, identifying a most severe class of severity or identifying a median or mode system fault severity. A compromised-system score or system fault may then be based on (for example) the severity-dependent counts, most sever severity, median severity or mode severity. One or more other metrics (e.g., identifying any mobility aid used by the client, patch used by the client and/or past or recent process received by the client) may further influence the compromised-system score or system fault.

At block 325, a result that is based on the compromised-system score or system fault is output. Outputting the result may include presenting the result (e.g., locally) and/or transmitting a communication that includes the result (e.g., to another device). The result may include the compromised-system score or system fault. The result may also include and/or may be associated with an identifier of the client. The result may indicate whether the client is or is predicted to be eligible for patch testing (e.g., as determined based on the compromised-system score or system fault). The result may identify a segmented group for the client that is identified or predicted based on the compromised-system score or system fault.

V.E. Example 1—Results

A set of 4,040 clients from the AOK PLUS database were identified as a set of MS clients. Using the RRMS inclusion and exclusion criteria, 1,394 clients from the AOK PLUS database were identified as being within the set of RRMS clients. For each client within the set of MS clients, keys generated using one or more codebooks and associated with session timestamps within a year preceding a time of MS root cause determination were characterized as corresponding to a "Baseline" time interval. Keys generated using the same or different one or more key books and associated with session timestamps within a year following a time of MS root cause determination were characterized as corresponding to a "Follow-Up" time interval. In some instances, the codebooks may be based on symmetric or asymmetric encryption protocols such as, but not limited to, RSA (e.g., such as advanced encryption standard or the like), Elliptic Curve Cryptography, a hash function (e.g., such as MD5, SHA-1, etc.), a substitution cipher, or the like.

Within each time interval, the keys were used to predict a higher level encoding of a compromised-system for the client in accordance with the criteria set forth in Table 6. Compromised-system scores for clients predicted to have the RRMS sub-type of MS (and thus being within the set of RRMS clients) were analyzed separately from compromised-system scores for clients predicted to have a non-RRMS sub-type of MS.

Figure 4:
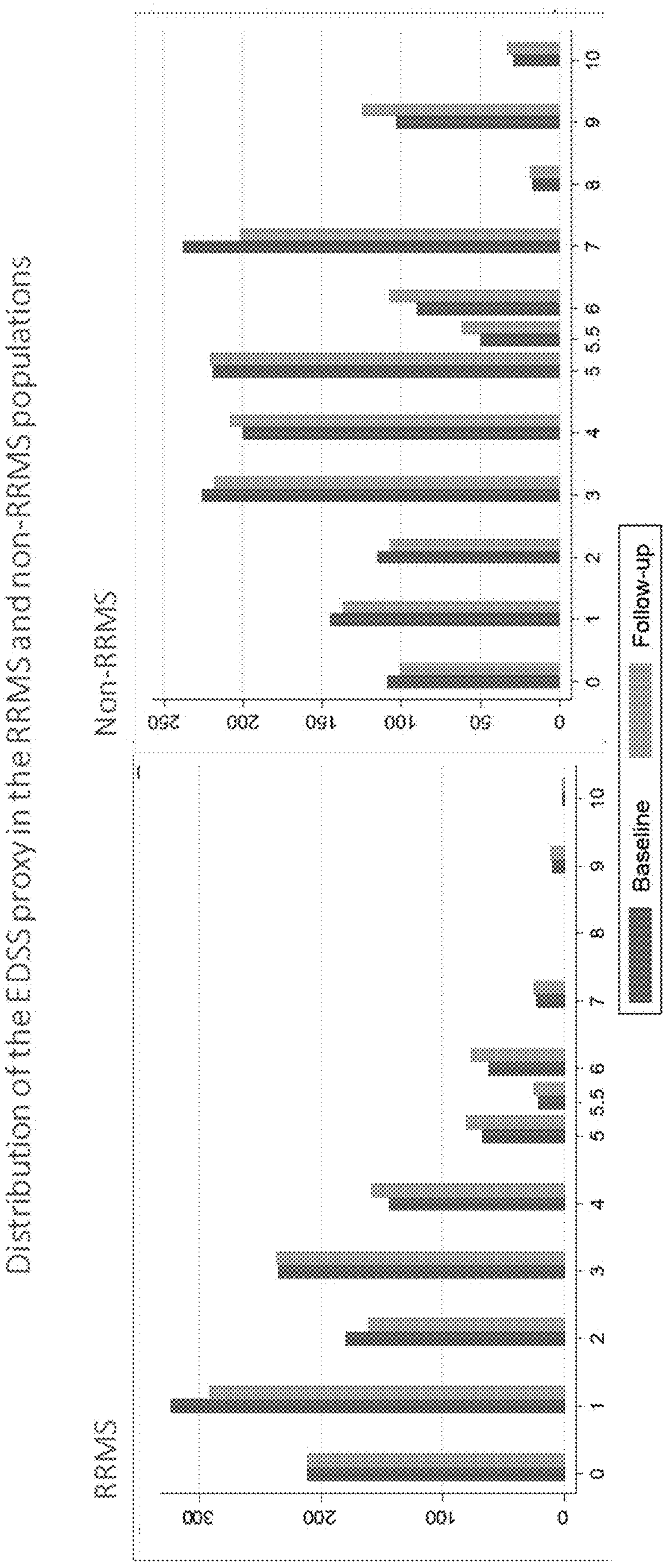
FIG. 4 shows exemplary distributions of higher level keys for an RRMS group and for a non-RRMS group generated for each of two time intervals using some techniques disclosed herein.

Table 5 shows statistics of the compromised-system scores for each group, and FIG. 4 shows distributions of the groups for the two MS sub-type groups. In general, compromised-system scores were higher for non-RRMS clients relative to RRMS clients, and compromised-system scores during the follow-up time interval were higher than baseline compromised-system scores.

TABLE 5

| | RRMS (N = 1,276) | | | Non-RRMS (N = 1,541) | | |
|---|---|---|---|---|---|---|
| | Baseline | Follow-Up | Difference | Baseline | Follow-Up | Difference |
| Mean (SD) | 2.4 (1.9) | 2.5 (2.0) | 0.1 (1.4) | 4.4 (2.6) | 4.5 (2.6) | 0.1 (1.8) |
| Median (IQR) | 2 (1-4) | 2 (1-4) | 0 (0-0) | 4 (3-7) | 4 (3-6) | 0 (0-0) |
| Min/Max | 0/10 | 0/10 | −7/7 | 0/10 | 0/10 | −8/8 |

Figure 5:
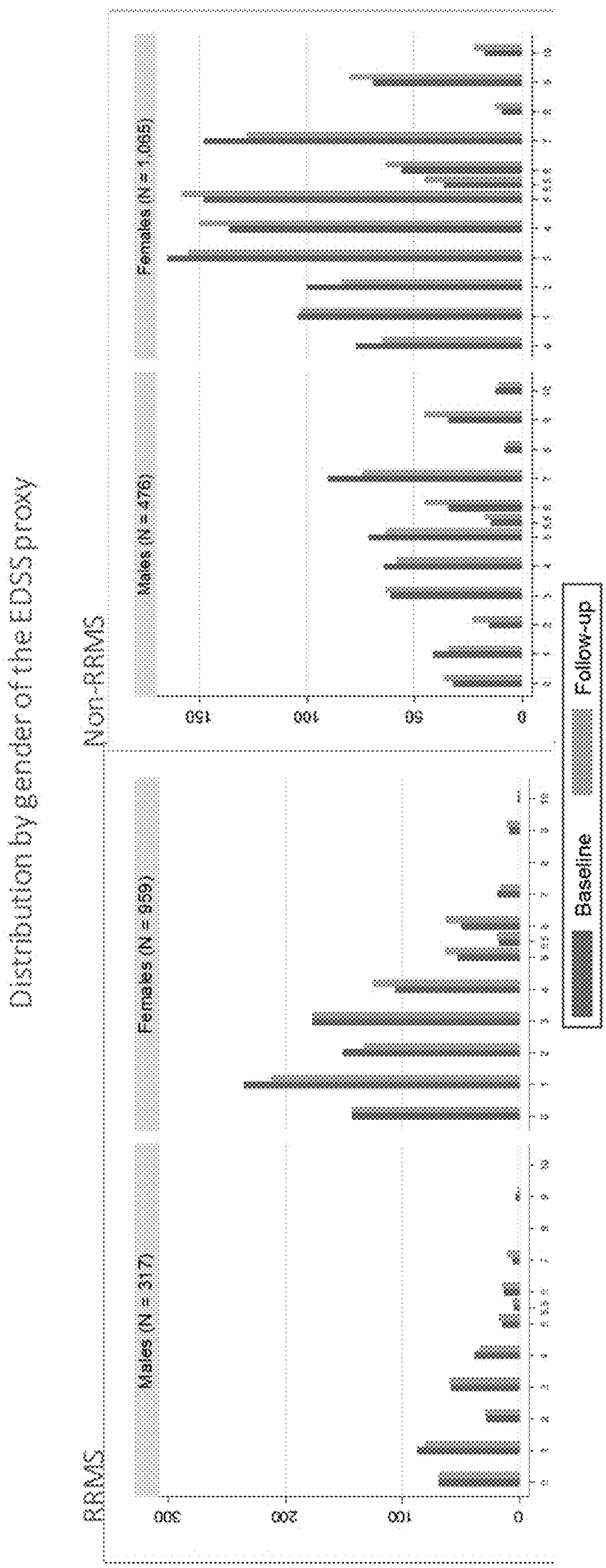
FIG. 5 shows a compromised-system-score distribution for each system corruption sub-type and for each gender, at baseline and follow-up using some techniques disclosed herein.

In one analysis, each client group was further divided into female and male clients. FIG. 5 shows a compromised-system-score distribution for each corruption sub-type and for each gender, at baseline and follow-up. The mean compromised-system score for females in the RRMS group was higher than males in the RRMS group as shown in Table 6 and Table 7.

TABLE 6

| | RRMS (N = 1,276) | | | | | |
|---|---|---|---|---|---|---|
| | Males (N = 317) | | | Females (N = 959) | | |
| | Baseline | Follow-Up | Difference | Baseline | Follow-Up | Difference |
| Mean (SD) | 2.2 (1.9) | 2.3 (2.0) | 0.1 (1.3) | 2.5 (1.9) | 2.6 (2.0) | 0.1 (1.4) |
| Median (IQR) | 2 (1-3) | 2 (1-4) | 0 (0-0) | 2 (1-4) | 2 (1-4) | 0 (0-0) |
| Min/Max | 0/9 | 0/9 | −5/7 | 0/10 | 0/10 | −7/6 |

TABLE 7

| | Non-RRMS (N = 1,541) | | | | | |
|---|---|---|---|---|---|---|
| | Males (N = 476) | | | Females (N = 1,065) | | |
| | Baseline | Follow-Up | Difference | Baseline | Follow-Up | Difference |
| Mean (SD) | 4.8 (2.6) | 4.8 (2.7) | 0 (1.9) | 4.2 (2.6) | 4.4 (2.6) | 0.2 (1.7) |
| Median (IQR) | 5 (3-7) | 5 (3-7) | 0 (0-0) | 4 (2-6) | 4 (3-6) | 0 (0-1) |
| Min/Max | 0/10 | 0/10 | −8/8 | 0/10 | 0/10 | −8/7 |

Figure 6:
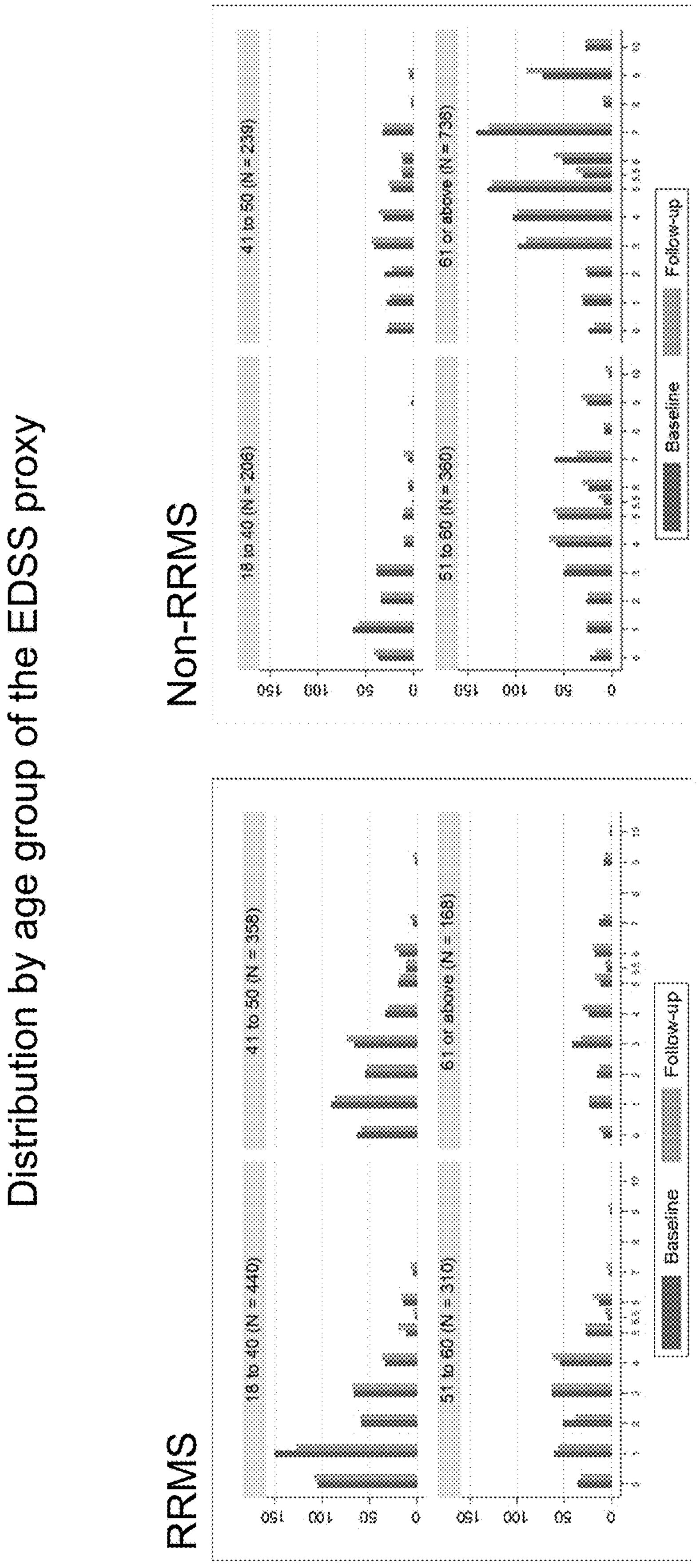
FIG. 6 shows a compromised-system-score distribution for each system corruption sub-type and for each temporal group, at baseline and follow-up using some techniques disclosed herein.

In one analysis, each client group was further divided into temporal groups: 18-40; 41-50; 51-60 and 61 and above. FIG. 6 shows a compromised-system-score distribution for each corruption sub-type and for each temporal group, at baseline and follow-up. In both the RRMS and non-RRMS groups, the mean compromised system score for clients over 60 was higher than mean scores for younger clients as shown in Tables 8-11.

TABLE 8

| | RRMS (N = 1,541) | | | | | |
|---|---|---|---|---|---|---|
| | 18-40 (N = 440) | | | 41-50 (N = 358) | | |
| | Baseline | Follow-Up | Difference | Baseline | Follow-Up | Difference |
| Mean (SD) | 1.7 (1.6) | 1.9 (1.7) | 0.2 (1.4) | 2.3 (1.9) | 2.4 (1.9) | 0.1 (1.2) |
| Median (IQR) | 1 (1-3) | 1 (1-3) | 0 (0-0) | 2 (1-3) | 2 (1-3) | 0 (0-1) |
| Min/Max | 0/7 | 0/7 | −7/6 | 0/9 | 0/9 | −4/7 |

TABLE 9

| | RRMS (N = 1,541) | | | | | |
|---|---|---|---|---|---|---|
| | 51-60 (N = 310) | | | >60 (N = 168) | | |
| | Baseline | Follow-Up | Difference | Baseline | Follow-Up | Difference |
| Mean (SD) | 2.6 (1.7) | 2.9 (1.9) | 0.3 (1.3) | 3.8 (2.3) | 3.7 (2.3) | −0.1 (1.7) |
| Median (IQR) | 3 (1-4) | 3 (1-4) | 0 (0-0) | 3 (2-5.5) | 4 (2-5) | 0 (0-0) |
| Min/Max | 0/9 | 0/9 | −5/6 | 0/10 | 0/10 | −7/6 |

TABLE 10

| | Non-RRMS (N = 1,541) | | | | | |
|---|---|---|---|---|---|---|
| | 18-40 (N = 206) | | | 41-50 (N = 239) | | |
| | Baseline | Follow-Up | Difference | Baseline | Follow-Up | Difference |
| Mean (SD) | 2.1 (1.9) | 2.1 (1.9) | 0 (1.4) | 3.6 (2.3) | 3.6 (2.3) | 0.1 (1.5) |
| Median (IQR) | 2 (1-3) | 2 (1-3) | 0 (0-1) | 3 (2-5) | 4 (2-5) | 0 (0-0) |
| Min/Max | 0/9 | 0/9 | −6/5 | 0/9 | 0/9 | −4/6 |

TABLE 11

| | Non-RRMS (N = 1,541) | | | | | |
|---|---|---|---|---|---|---|
| | 51-60 (N = 360) | | | >60 (N = 736) | | |
| | Baseline | Follow-Up | Difference | Baseline | Follow-Up | Difference |
| Mean (SD) | 4.5 (2.4) | 4.6 (2.4) | 0.1 (1.8) | 5.2 (2.4) | 5.3 (2.4) | 0.1 (1.9) |
| Median (IQR) | 4 (3-7) | 5 (3-6) | 0 (0-0.75) | 5 (4-7) | 5 (4-7) | 0 (0-0.25) |
| Min/Max | 0/10 | 0/10 | −8/8 | 0/10 | 0/10 | −8/8 |

The higher level encodings representing predicted compromised system scores generated based on keys successfully captured general trends observed in the patch testing. For example, compromised system scores at follow-up were higher than at baseline, and older clients had higher compromised system scores. Thus, the automated processing of keys may facilitate more routine and more objective assessments of clients' compromised systems relative to traditional human-based-assessment approaches.

The invention claimed is:

1. A computer-implemented method comprising:

transmitting, to a remote database storing support-system authentication request data, a communication requesting support-system authentication request data associated with a set of subjects diagnosed with or suspected of having multiple sclerosis (MS), wherein the communication comprises a query represented with a structured syntax;

receiving, from the remote database, a response that includes the support-system authentication request data associated with each subject of the set of subjects;

for each subject of the set of subjects, extracting, using a key processor, a set of keys from the support-system authentication request data associated with the subject, each key of the set of keys having a particular syntax corresponding to the structured syntax of the query and characterizing a MS system fault or a root cause determination of a set of MS system faults;

allocating, using the key processor, each key of the set of keys to a class corresponding to a fault severity based on the particular syntax using a first codebook, wherein the first codebook associates each of multiple MS system fault keys with a fault severity class, and the multiple MS system fault keys comprise the set of keys;

determining, using the key processor based on data associated with the subject, one or more multiple-sclerosis-related system fault therapies used by the subject to address the MS system fault or the root cause determination of the set of MS system faults;

determining, using a state decryption system, a MS compromised system score and/or a MS system fault identifier based at least in part on the class corresponding to the fault severity of each key of the set of keys and the one or more multiple-sclerosis-related system fault therapies used by the subject using a second codebook, wherein:

(i) the MS compromised system score indicates one or more processes of the subject that are disabled or that have modified functionality, (ii) the MS system fault identifier identifies a particular MS system fault, a particular MS corruption, or a sub-type of the particular MS system fault, and (iii) the second codebook comprises one or more higher level encodings of the multiple MS system fault keys in the first codebook, wherein the second codebook comprises a multi-dimensional mapping that combines a plurality of heterogeneous features to generate the MS compromised system score and/or the MS system fault identifier for each subject, wherein the plurality of heterogeneous features comprises at least inpatient and outpatient diagnoses, outpatient multiple-sclerosis-related system fault therapy authorizations, inpatient and outpatient operations and procedures, medical aids, special therapies, and dates or periods of diagnosis; and determining, using the state decryption system, a segmented group to which the subject is to be assigned based on the MS compromised system score and/or the MS system fault identifier, wherein each subject assigned to the segmented group has a same eligibility or ineligibility for a MS corruption-modifying therapy, or a same response to the a MS corruption-modifying therapy; and administering the MS corruption-modifying therapy to a subject within a subset of subjects, wherein each subject of the subset of subjects is assigned to a same segmented group corresponding to a progressive subtype of MS.

2. The computer-implemented method of claim 1, further comprising:

determining, using the state decryption system, one or more access requirements for the MS corruption-modifying therapy; and determining that the subject satisfies the one or more access requirements to be added to the segmented group based on the MS compromised system score and/or the MS system fault identifier.

3. The computer-implemented method of claim 2, further comprising:

in response to determining that the subject satisfies the one or more access requirements, allocating the subject to a first subset of the segmented group that is configured for a first sub-process of the MS corruption-modifying therapy, wherein two or more subjects of the first subset of the segmented group include a same MS compromised system score and/or a same MS system fault identifier; and defining a second subset of the segmented group that is configured for a second sub-process of the MS corruption-modifying therapy, wherein the first subset of the segmented group and a second subset of the segmented group are disjoint sets, and wherein the computer-implemented method is configured to compare results of the first subset of the segmented group and the second subset of the segmented group.

4. The computer-implemented method of claim 1, wherein the MS compromised system score is determined, further comprising: for each subject of the set of subjects, identifying, using the key processor or the state decryption system, one or more additional keys associated with the subject;

determining, using the state decryption system based on the one or more additional keys and at least one of the set of keys, another MS compromised system score of the subject, wherein the MS compromised system score is associated with a first time and the other MS compromised system score is associated with a second time; and determining, using the state decryption system, a progression based on the MS compromised system score and the other MS compromised system score.

5. The computer-implemented method of claim 4, further comprising:

determining, using the state decryption system, one or more metrics characterizing an efficacy of the MS corruption-modifying therapy based on the progression and a set of other progressions associated with other subjects in the segmented group.

6. The computer-implemented method of claim 1, wherein the MS compromised system score is determined, further comprising:

executing a regression test using the set of keys, the regression test including:

identifying a second MS compromised system score based on one or more first keys of the set of keys; and identifying a third MS compromised system score based on one or more second keys of the set of keys; and defining the MS compromised system score to be a maximum of the second MS compromised system score and the third MS compromised system score.

7. The computer-implemented method of claim 1, wherein the MS compromised system score corresponds to an Expanded Disability Status Scale (EDSS) score.

8. The computer-implemented method of claim 1, wherein the support-system authentication request data is encoded using an encryption system that generates encryption keys using a version of an International Classification of Diseases (ICD) codebook, and wherein each key in the set of keys is an encryption key of the encryption keys.

9. A system comprising:

one or more processors, wherein the one or more processors comprise a key processor;

a remote database; and a non-transitory computer-readable medium storing instructions that, when executed by the one or more processors, cause the one or more processors to perform operation including:

transmitting, to a remote database storing support-system authentication request data, a communication requesting support-system authentication request data associated with a set of subjects diagnosed with or suspected of having multiple sclerosis (MS), wherein the communication comprises a query represented with a structured syntax;

receiving, from the remote database, a response that includes the support-system authentication request data associated with each subject of the set of subjects;

for each subject of the set of subjects, extracting, using a key processor, a set of keys from the support-system authentication request data associated with the subject, each key of the set of keys having a particular syntax corresponding to the structured syntax of the query and characterizing a MS system fault or a root cause determination of a set of MS system faults;

allocating, using the key processor, each key of the set of keys to a class corresponding to a fault severity based on the particular syntax using a first codebook, wherein the first codebook associates each of multiple MS system fault keys with a fault severity class, and the multiple MS system fault keys comprise the set of keys;

determining, using the key processor based on data associated with the subject, one or more multiple-sclerosis-related system fault therapies used by the subject to address the MS system fault or the root cause determination of the set of MS system faults;

determining, using a state decryption system, a MS compromised system score and/or a MS system fault identifier based at least in part on the class corresponding to the fault severity of each key of the set of keys and the one or more multiple-sclerosis-related system fault therapies used by the subject using a second codebook, wherein:

(i) the MS compromised system score indicates one or more processes of the subject that are disabled or that have modified functionality, (ii) the MS system fault identifier identifies a particular MS system fault, a particular MS corruption, or a sub-type of the particular MS system fault, and (iii) the second codebook comprises one or more higher level encodings of the multiple MS system fault keys in the first codebook, wherein the second codebook comprises a multi-dimensional mapping that combines a plurality of heterogeneous features to generate the MS compromised system score and/or the MS system fault identifier for each subject, wherein the plurality of heterogeneous features comprises at least inpatient and outpatient diagnoses, outpatient multiple-sclerosis-related system fault therapy authorizations, inpatient and outpatient operations and procedures, medical aids, special therapies, and dates or periods of diagnosis; and determining, using the state decryption system, a segmented group to which the subject is to be assigned based on the MS compromised system score and/or the MS system fault identifier, wherein each subject assigned to the segmented group has a same eligibility or ineligibility for a MS corruption-modifying therapy, or a same response to theMS corruption-modifying therapy; and triggering the administration of the MS corruption-modifying therapy to a subject within a subset of subjects, wherein each subject of the subset of subjects is assigned to a same segmented group corresponding to a progressive sub-type of MS.

10. The system of claim 9, wherein the first codebook further associates each of multiple MS system fault keys with one or more words, one or more observations, and/or one or more root cause determination.

11. The system of claim 9, wherein the first codebook and/or the second codebook is encrypted using symmetric or asymmetric encryption protocols.

12. The system of claim 9, wherein the second codebook comprises higher level encodings corresponds to a prediction that the subject has the particular MS system fault based on criteria comprising (i) a root cause determination of the particular MS system fault within a first predetermined time interval, (ii) a multiple-sclerosis-related system fault therapy administration record corresponding to the particular MS system fault within the first predetermined time interval, (iii) a medical image scan record within the first predetermined time interval, (iv) a root cause determination of a system fault related to the particular MS system fault within a first predetermined time interval, (v) a multiple-sclerosis-related system fault therapy administration record corresponding to the system fault related to the particular MS system fault within the first predetermined time interval, (vi) a root cause determination of the particular MS system fault within a second predetermined time interval, wherein the second predetermined time interval is ahead of time than the first predetermined time interval, or (vii) any combination of (i)-(vi).

13. The system of claim 9, wherein the one or more higher level encodings represents (i) the particular MS system fault, (ii) the sub-type of the particular MS system fault, (iii) the modified functionality, (iv) a MS corruption-modifying therapy eligibility, and/or (v) a segmented group.

14. The system of claim 9, wherein the first codebook is configured such that information is lost during encoding of the first codebook, and the second codebook associates particular combination of the keys of the multiple MS system fault keys in the first codebook to capture at least in part of the lost information.

15. The system of claim 9, wherein the one or more processors are further caused to perform operation including:

determining, using the state decryption system, one or more access requirements for the MS corruption-modifying therapy;

for each subject of the set of subjects, determining, using the state decryption system, based on data associated with the subject, one or more multiple-sclerosis-related system fault therapies used by the subject to address the MS system fault or the root cause determination of the set of MS system faults, wherein the generating the MS compromised system score or the MS system fault identifier is further based on the one or more multiple-sclerosis-related system fault therapies used by the subject; and determining, based on the MS compromised system score or the MS system fault identifier, that the subject satisfies the one or more access requirements to be added to the segmented group.

16. The computer-implemented method of claim 1, further comprising accessing the support-system authentication request data associated with the set of subjects, wherein the support-system authentication request data is encoded by an encryption system, wherein the support-system authentication request data is encoded using an encryption system that generates encryption keys.

17. The system of claim 9, wherein the one or more processors are further caused to perform operation including accessing the support-system authentication request data associated with the set of subjects, wherein the support-system authentication request data is encoded by an encryption system, wherein the support-system authentication request data is encoded using an encryption system that generates encryption keys.

18. The computer-implemented method of claim 1, wherein the MS corruption-modifying therapy is selected from the group consisting of Alemtuzumab, Cladribine, Daclizumab, Dimethyl fumarate, Fingolimod, Glatiramer acetate, Interferon-beta-1a, Interferon-beta-1b, Natalizumab, Ocrelizumab, Peginterferon beta-1a, and Teriflunomide.

19. The system of claim 9, wherein the MS corruption-modifying therapy is selected from the group comprising Alemtuzumab, Cladribine, Daclizumab, Dimethyl fumarate, Fingolimod, Glatiramer acetate, Interferon-beta-1a, Interferon-beta-1b, Natalizumab, Ocrelizumab, Peginterferon beta-1a, and Teriflunomide.

* * * * *